United States Patent
Hodgson et al.

(10) Patent No.: US 9,677,104 B2
(45) Date of Patent: Jun. 13, 2017

(54) EXPRESSION PROCESS

(75) Inventors: Ian John Hodgson, Billingham (GB); Tibor Nagy, Billingham (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 0 days.

(21) Appl. No.: 13/996,364

(22) PCT Filed: Dec. 10, 2011

(86) PCT No.: PCT/GB2011/001725
§ 371 (c)(1),
(2), (4) Date: Jun. 20, 2013

(87) PCT Pub. No.: WO2012/085496
PCT Pub. Date: Jun. 28, 2012

(65) Prior Publication Data
US 2013/0273605 A1    Oct. 17, 2013

(30) Foreign Application Priority Data
Dec. 21, 2010   (GB) .................................. 1021795.8

(51) Int. Cl.
*C12N 15/67* (2006.01)
*C12P 21/00* (2006.01)
*C12N 15/70* (2006.01)

(52) U.S. Cl.
CPC .............. *C12P 21/00* (2013.01); *C12N 15/67* (2013.01); *C12N 15/70* (2013.01)

(58) Field of Classification Search
None
See application file for complete search history.

(56) References Cited

U.S. PATENT DOCUMENTS

| 6,537,779 B1 * | 3/2003 | Kara et al. | 435/69.1 |
| 2009/0170160 A1 * | 7/2009 | Kara et al. | 435/69.1 |

FOREIGN PATENT DOCUMENTS

| WO | 03/068978 | 8/2003 |
| WO | 2005/061716 | 7/2005 |
| WO | 2006/029985 | 3/2006 |
| WO | 2007/088371 | 8/2007 |
| WO | 2008/139153 | 11/2008 |

OTHER PUBLICATIONS

Baneyx, Current Opinion in Biotechnology, 1999, vol. 10, pp. 411-421.*
Krause, Identification of a Multimer Resolution System Involved in Stabilization of the *Salmonella* Dublin Virulence Plasmid pSDL2, Journal of Bacteriology, 173, pp. 5754-5762, 1991.
Sinden, Perfect Palindromic Lac Operator DNA Sequence Exists as a Stable Cruciform Structure in Supercoiled DNA in Vitro But not in Vivo, Proceedings of the National Academy of Sciences of the United States of America, 80, pp. 1797-1801, 1983.

* cited by examiner

*Primary Examiner* — Mindy G Brown
(74) *Attorney, Agent, or Firm* — Morgan, Lewis & Bockius LLP (57) ABSTRACT

A process for the production of a target recombinant polypeptide is provided. The process comprises expressing a vector comprising a promoter operatively linked to an expression cassette for the target recombinant polypeptide; and a perfect palindrome operator sequence in a culture medium, wherein the culture medium is substantially free from antibiotic.

20 Claims, 1 Drawing Sheet

Figure 1

Figure 2

SEQUENCE LISTING

<160> NUMBER OF SEQ ID NOS: 5

<210> SEQ ID NO 1
<211> LENGTH: 540
<212> TYPE: DNA
<213> ORGANISM: Homo sapiens

<400> SEQUENCE: 1

| | | | | | | |
|---|---|---|---|---|---|---|
| catatgactc | cactgggtcc | tgcttcttct | ctgcctcaat | cttttctgct | gaaatgtctg | 60 |
| gaacaggttc | gtaaaatcca | gggtgatggt | gcggcactgc | aggagaaact | gtgcgcgacg | 120 |
| tacaaactgt | gccacccgga | ggagctggtt | ctgctgggcc | actccctggg | catcccatgg | 180 |
| gcaccgctgt | cctcttgccc | gtctcaggcc | ctgaactgg | caggttgcct | gtctcagctg | 240 |
| cactctggcc | tgttcctgta | tcagggtctg | ctgcaagcgc | tggaaggcat | tccccggaa | 300 |
| ctgggtccga | ccctggacac | cctgcagctg | gacgtcgcgg | acttcgcaac | gaccatctgg | 360 |
| cagcagatgg | aagagctggg | tatggctccg | gcactgcagc | cgactcaggg | tgcaatgccg | 420 |
| gcctttgcca | gcgcgttcca | gcgccgtgct | ggcggtgtac | tggttgcgtc | tcacctgcag | 480 |
| tcttttctgg | aggtttccta | ccgcgtgctg | cgccatctgg | ctcagccttg | ataactcgag | 540 |

<210> SEQ ID NO 2
<211> LENGTH: 591
<212> TYPE: DNA
<213> ORGANISM: Homo sapiens

<400> SEQUENCE: 2

| | | | | | | |
|---|---|---|---|---|---|---|
| catatgtttc | caactatccc | actgtctcgt | ctgtttgata | atgctatgct | gcgcgcccac | 60 |
| cgtctgcatc | aactggcctt | cgatacctac | caggaatttg | aggaggcgta | cattccaaaa | 120 |
| gaacagaaat | actcttttcct | gcagaatccg | cagacctctc | tgtgcttcag | cgaatccatc | 180 |
| cctactcctt | ctaaccgcga | ggaaacccag | caaaagagca | acctggaact | gctgcgtatc | 240 |
| tccctgctgc | tgatccagag | ctggctggag | ccggttcagt | ttctgcgttc | cgtgttcgcg | 300 |
| aattccctgg | tgtatggcgc | ctccgactcc | aacgtttacg | acctgctgaa | agacctggaa | 360 |
| gagggcatcc | agactctgat | gggccgtctg | gaggacggct | cccctcgtac | cggccagatc | 420 |
| ttcaaacaaa | cctacagcaa | atttgatacc | aacagccaca | atgacgacgc | tctgctgaaa | 480 |
| aactacggcc | tgctgtactg | tttccgcaag | gatatggata | aagtagaaac | ctttctgcgc | 540 |
| atcgttcaat | gtcgcagcgt | ggaaggtagc | tgcggcttct | gataactcga | g | 591 |

<210> SEQ ID NO 3
<211> LENGTH: 1563
<212> TYPE: DNA
<213> ORGANISM: Escherichia coli

<400> SEQUENCE: 3

| | | | | | | |
|---|---|---|---|---|---|---|
| cctgagcgca | tgttcatcat | cagtaacccg | tatcgtgagc | atcctctctc | gtttcatcgg | 60 |
| tatcattacc | cccatgaaca | gaaatccccc | ttacacggag | gcatcagtga | ccaaacagga | 120 |
| aaaaaccgcc | cttaacatgg | cccgctttat | cagaagccag | acattaacgc | ttctggagaa | 180 |
| actcaacgag | ctggacgcgg | atgaacaggc | agacatctgt | gaatcgcttc | acgaccacgc | 240 |
| tgatgagctt | taccgcagct | gcctcgcgcg | tttcggtgat | gacggtgaaa | acctctgaca | 300 |
| catgcagctc | ccggagacgg | tcacagcttg | tctgtaagcg | gatgccggga | gcagacaagc | 360 |
| ccgtcagggc | gcgtcagcgg | gtgttggcgg | gtgtcgggc | gcagccatga | cccagtcacg | 420 |
| tagcgatagc | ggagtgtata | ctggcttaac | tatgcggcat | cagagcagat | tgtactgaga | 480 |

```
gtgcaccata tgcggtgtga aataccgcac agatgcgtaa ggagaaaata ccgcatcagg    540
cgctcttccg cttcctcgct cactgactcg ctgcgctcgg tcgttcggct gcggcgagcg    600
gtatcagctc actcaaaggc ggtaatacgg ttatccacag aatcagggga taacgcagga    660
aagaacatgt gagcaaaagg ccagcaaaag gccaggaacc gtaaaaaggc cgcgttgctg    720 gcgttttttcc ataggctccg cccccctgac gagcatcaca aaaatcgacg ctcaagtcag    780
aggtggcgaa acccgacagg actataaaga taccaggcgt ttccccctgg aagctccctc    840
gtgcgctctc ctgttccgac cctgccgctt accggatacc tgtccgcctt tctcccttcg    900
ggaagcgtgg cgctttctca tagctcacgc tgtaggtatc tcagttcggt gtaggtcgtt    960
cgctccaagc tgggctgtgt gcacgaaccc ccgttcagc ccgaccgctg cgccttatcc    1020
ggtaactatc gtcttgagtc aacccggta agacacgact tatcgccact ggcagcagcc    1080
actggtaaca ggattagcag agcgaggtat gtaggcggtg ctacagagtt cttgaagtgg    1140
tggcctaact acggctacac tagaaggaca gtatttggta tctgcgctct gctgaagcca    1200
gttaccttcg gaaaaagagt tggtagctct tgatccggca acaaaccac cgctggtagc    1260 ggtggttttt ttgtttgcaa gcagcagatt acgcgcagaa aaaaggatc tcaagaagat    1320 cctttgatct tttctacggg gtctgacgct cagtggaacg aaaactcacg ttaagggatt    1380
ttggtcatga gattatcaaa aaggatcttc acctagatcc ttttaaatta aaaatgaagt    1440
tttaaatcaa tctaaagtat atatgagtaa acttggtctg acagttacca atgcttaatc    1500
agtgaggcac ctatctcagc gatctgtcta tttcgttcat ccatagttgc ctgactcccc    1560
gtc                                                                   1563

<210> SEQ ID NO 4
<211> LENGTH: 931
<212> TYPE: DNA
<213> ORGANISM: Escherichia coli

<400> SEQUENCE: 4
cctgagcgcg ctagcggagt gtatactggc ttactatgtt ggcactgatg agggtgtcag     60
tgaagtgctt catgtggcag gagaaaaaag gctgcaccgg tcgtcagca gaatatgtga    120 tacaggatat attccgcttc ctcgctcact gactcgctac gctcggtcgt tcgactgcgg    180
cgagcggaaa tggcttacga acggggcgga gatttcctgg aagatgccag gaagatactt    240
aacagggaag tgagagggcc gcggcaaagc cgttttttcca taggctccgc cccctgaca    300 agcatcacga aatctgacgc tcaaatcagt ggtggcgaaa cccgacagga ctataaagat    360
accaggcgtt tcccctggcg gctccctcgt gcgctctcct gttcctgcct ttcggtttac    420
cggtgtcatt ccgctgttat ggccgcgttt gtctcattcc acgcctgaca ctcagttccg    480
ggtaggcagt tcgctccaag ctggactgta tgcacgaacc cccgttcag tccgaccgct    540 gcgccttatc cggtaactat cgtcttgagt ccaacccgga agacatgca aaagcaccac    600 tggcagcagc cactggtaat tgatttagag gagttagtct tgaagtcatg cgccggttaa    660
ggctaaactg aaaggacaag ttttggtgac tgcgctcctc caagccagtt acctcggttc    720
aaagagttgg tagctcagag aaccttcgaa aaaccgccct gcaggcggt ttttcgttt    780 tcagagcaag agattacgcg cagaccaaaa cgatctcaag aagatcatct tattaatcag    840
ataaaatatt tctagatttc agtgcaattt atctcttcaa atgtagcacc tgaagtcagc    900
cccatacgat ataagttgta gactccccgt c                                   931
```

```
<210> SEQ ID NO 5
<211> LENGTH: 656
<212> TYPE: DNA
<213> ORGANISM: Artificial Sequence
<220> FEATURE:
<223> OTHER INFORMATION: Vector backbone section used in Examples 7 and
      8

<400> SEQUENCE: 5 cccgggcat  gaccgtcgtc  gccgccctga  tggcggtctt  cttcatcatg  caacttgtcg    60
gacaggtgcc  ggccgcgctt  tgggtcattt  tcggcgagga  tcgctttcac  tgggacgcga   120
ccacgatcgg  catttcgctt  gccgcatttg  gcattctgca  ttcactcgcc  caggcaatga   180
tcaccggccc  tgtagccgcc  cggctcggcg  aaaggcgggc  actcatgctc  ggaatgattg   240
ccgacggcac  aggctacatc  ctgcttgcct  tcgcgacacg  gggatggatg  gcgttcccga   300
tcatggtcct  gcttgcttcg  ggtggcatcg  gaatgccggc  gctgcaagca  atgttgtcca   360
ggcaggtgga  tgaggaacgt  cagggggcagc  tgcaaggctc  actggcggcg  ctcaccagcc   420
tgacctcgat  cgtcggaccc  ctcctcttca  cggcgatcta  tgcggcttct  ataacaacgt   480
ggaacgggtg  ggcatggatt  gcaggcgctg  ccctctactt  gctctgcctg  ccggcgctgc   540
gtcgcgggct  ttggagcggc  gcagggcaac  gagccgatcg  ctgatcgtgg  aaacgatagg   600
cctccatgtg  ggaattgtga  gcgctcacaa  ttccaagaac  aatcctgcac  gaattc       656
```

EXPRESSION PROCESS

SEQUENCE LISTING SUBMISSION VIA EFS-WEB

A computer readable text file, entitled "056258-5146_SequenceListing.txt," created on or about 20 Jun. 2013, with a file size of about 7 kb contains the sequence listing for this application and is hereby incorporated by reference in its entirety.

The present invention concerns a process for expressing recombinant polypeptides.

The manufacture of polypeptides by recombinant technology has proven to be an effective and versatile method, especially when the host organism is E. coli. However, cells which express the gene encoding the desired recombinant polypeptide have an additional metabolic burden compared with cells which do not express that gene. This means that the desired recombinant cells are at a competitive disadvantage, and unless steps are taken to redress this, are rapidly eliminated from the culture, thus rendering the production process ineffective. One common method of providing cells containing the gene encoding the desired polypeptide with a selective advantage is to include a gene conferring antibiotic resistance on the same vector. In the presence of the appropriate antibiotic, such as kanamycin or tetracycline, only those cells having the antibiotic resistance gene, and therefore capable of expressing the desired polypeptide, can survive.

Recently, there have been concerns about the excessive use of antibiotics. It is therefore desirable to identify stable protein expression processes which do not require the use of antibiotics.

According to one aspect of the present invention, there is provided a process for the production of a target recombinant polypeptide which comprises expressing a vector comprising:
 a) a promoter operatively linked to an expression cassette for the target recombinant polypeptide; and
 b) a perfect palindrome operator sequence;
in a culture medium, wherein the culture medium is substantially free from antibiotic.

Operator sequences which may be employed in the expression system according to the present invention include lac, gal, deo and gln. One or more perfect palindrome operator sequences may be employed. In many preferred embodiments, two perfect palindrome operator sequences are employed, most advantageously one operator sequence being located downstream of the promoter, and one operator sequence being located upstream of the promoter. When two operator systems are employed, the operator sequences are preferably spaced to maximise control of the promoter. In many embodiments, the spacing is from 85 to 150 base pairs apart, preferably from 90 to 126 base pairs apart, and most preferably 91 or 92 base pairs apart. In certain embodiments, an operator sequence overlaps with the transcriptional start point It will be recognised that the operator system is commonly employed with an appropriate repressor sequence. Repressor sequences produce repressor protein, for example lacI gene sequence when using the lac operators. Other lac repressor sequences may also be used, for example the lacI$^Q$ sequence can be used to increase the level of lac repressor protein. The repressor sequence may also be provided by the host cell genome or by using an additional compatible plasmid. Preferably the repressor sequence is present on the same vector as the operator sequence(s). In certain embodiments, the repressor sequence, especially a lacI repressor sequence, is incorporated on the vector in the opposite orientation to transcription of the expression cassette for the target polypeptide.

Promoters which may be employed in the vectors according to the present invention comprise constitutive or inducible promoters. It will be recognised that promoters are generally selected from promoters known to be effective in the host cell. For example, E. coli promoters are commonly employed in E. coli host cells, mammalian promoters in mammalian cells, yeast promoters in yeast cells. It will be recognised that many promoters from prokaryotic hosts can be employed in eukaryotic hosts, and vice versa.

In many preferred embodiments, the promoter is a prokaryotic promoter. Examples of prokaryotic promoters that can be employed include:
 a) phage RNA polymerase-dependent promoters, particularly T7 RNA polymerase-dependent promoter systems, preferably single T7 promoters, including those disclosed by Studier and Moffat, J. Mol. Biol. 189:113-130 (1986), incorporated herein by reference, especially a T7 gene 10 promoter; and
 b) host RNA polymerase-based promoter systems, especially E. coli RNA polymerase-based promoter systems.

When a T7 RNA-polymerase dependent promoter system is employed, it will be recognised that a source of T7 RNA polymerase is required, which is provided by methods known in the art, and commonly by inserting a λDE3 prophage expressing the required phage polymerase into the host strain to create lysogenic host strains. The T7 RNA polymerase can also be delivered to the cell by infection with a specialised λ transducing phage that carries the gene for the T7 RNA polymerase.

Examples of constitutive promoters which can be employed in aspects of the present invention include T7A1, T7A2, T7A3, spc ribosomal protein operon promoter, β-lactamase gene promoter, $P_L$ promoter of phage λ, replication control promoters $P_{RNAI}$ and $P_{RNAII}$, P1 and P2 promoter of the rrnB ribosomal RNA operon, Lac repressor protein promoter pLacI, glyceraldehyde phosphate dehydrogenase (GAPDH) and plasma membrane H(+)-ATPase (PMA1) promoter, mating factor (MF)-α promoter, KEX2, TEF-1, simian virus 40 (SV40) early promoter, rous sarcoma virus (RSV) promoter, cytomegalovirus (CMV) promoter, and human β-actin promoter. Further examples of constitutive promoters include inducible promoters which have been modified to remove the control region, for example lac or lac promoters modified to remove the lac or tac operators. Constitutive promoters can be modified to form inducible promoter systems by the addition of control regions, such as operator sequences.

Examples of inducible promoters which can be employed include lac, lacUV5, trp, tac, trc, phoA, arabinose inducible promoters, temperature inducible promoters (both high and low temperature), copper inducible promoters, uspA, uspB, malK, osmotic pressure-inducible promoters, galactose inducible promoters, pheromone inducible promoters, glucoamylase promoter, tetracycline responsive promoters, human c-fos promoter, ecdysone-inducible promoter, and glucocorticoid-inducible promoters.

Examples of preferred promoters which can be employed include T7 gene 10 promoter, T7A1, T7A2, T7A3, λpL, λpR, lac, lacUV5, trp, tac, trc, phoA and rrnB, each of which being employed in an inducible system, with inducible promoter systems comprising T7A3, tac, lac and λpL promoters being especially preferred The vectors employed in the present invention comprise an origin of replication ("ORI") appropriate to the host cell. ORIs which can be employed for given host cells are well known in the art. Preferred ORIs for use in *E. coli* are colE1 ORIs, for example pBR322, pAT, pUC, p15a ORIs; ColA ORIs, CloDF13 ORIs and RSF1030 ORIs. ORIs that can be employed with Pseudomonads, such as *Ps. fluorescens* and *Ps. putida* include pPS10 and pVS1. ORIs that can be employed with yeasts include 2 micron and YCp yeast centromere plasmid vectors. ORIs that can be employed with mammalian cells, such as CHO cells, include the SV-40 replication origin and EBV origin and EBNA system. In many preferred embodiments, the host cell is *E. coli*, and the ORI is a colE1 ORI, and especially pAT153.

In many preferred embodiments of the present invention, the vectors comprise a plasmid stability locus, particularly a multimer resolution system, including ckr (originally derived from plasmid ColK), parCBA (originally derived from plasmid RK2), par (originally derived from plasmid RP4) and preferably a cer stability sequence.

Vectors employed in the process according to the present invention preferably comprise one or more terminator sequences. Examples of such terminator sequences are well known in the art for the host cell employed. Preferred terminator sequences for bacterial host cells, especially for *E. coli*, include T7 terminator sequences and T4 terminator sequences. In certain preferred embodiments, a terminator sequence, especially a T7 terminator sequence, is located downstream of the expression cassette for the target polypeptide, and positioned so as to prevent transcriptional read-through after transcription of the expression cassette. In certain highly preferred embodiments, a terminator sequence, especially a T4 terminator sequence, is located upstream of the promoter operably linked to the expression cassette for the target polypeptide, to prevent transcriptional read-through from upstream of the promoter. In such embodiments, and where an operator sequence is also present upstream of the promoter, the terminator sequence is preferably located upstream of this operator sequence.

Although the process of the present invention expresses the expression cassette for the target recombinant polypeptide in a culture medium in the absence of antibiotic selection pressure, the vectors employed may comprise an antibiotic selection marker. Such selection markers are beneficial during transfection of host cells, in order to select cells which have incorporated the vector expressing the target polypeptide. Examples of antibiotic selection markers which can be present include the kanamycin resistance gene, inducible tetracycline resistance gene (tetA/tetR) system as described in EP-A-0502637, the ampicillin resistance gene, the chloramphenicol resistance gene and the neomycin resistance gene. Alternatively, non-antibiotic selection markers can be employed. Examples of non-antibiotic selection markers include auxotrophic markers, such as proline or glycine-auxotrophy systems, see for example Fiedler et al, Gene, 2001, 274:111-8 and Vidal et al, J Biotechnol, 2008, 134:127-36, and the use of complementary essential genes on vectors in strains where the essential gene has been made defective, such as dapD-gene systems, see for example Degryse E et al, J Biotechnol, 1991, 18:29-39 and Cranenburgh et al Nucleic Acids Res, 2001, 29:E26, and infA gene systems, see for example Hagg et al, J Biotechnol 2004, 111:17-30. Other non-antibiotic systems include heavy metal resistance such as cadmium and copper resistance, which may be suitable where the possible presence of traces of such metals are acceptable.

Vectors employed in the process of the present invention may also incorporate a signal sequence if secretion of the desired protein is required, such signal sequence preferably being incorporated in the expression cassette for the target polypeptide.

The expression vector employed in the process of the present invention may be integrated into the host cell genome, but is preferably comprised within an extrachromosomal element such as a plasmid. Alternatively, the expression vector may be incorporated into phage or viral vectors and these used to deliver the expression system into the host cell system. The expression vectors can be assembled by methods known in the art.

The process of the present invention is employed to produce recombinant polypeptides in host cells, and especially in microorganisms. As used herein, "polypeptides" refers generally to peptides and proteins having more than about 10 amino acids. The host cell may be prokaryotic or eukaryotic. Examples of prokaryotic cells include bacterial cells, for example gram-negative bacterial cells, including *E. coli, Salmonella typhimurium, Serratia marsescens* and *Pseudomonas aeruginosa*, and gram-positive bacterial cells including *Bacillus subtilis*. Examples of eukaryotic cells include yeasts, such as *Pichia pastoris, Saccharomyces cerevisiae, Hansenula polymorpha, Kluyveromyces lactis, Schizosaccharomyces pombe*. Mammalian host cells which can be employed include human cell lines, such as human embryonic kidney and PERC.6 cells; murine cell lines, such as NS0 cells; and particularly hamster cell lines such as baby hamster kidney cells and especially Chinese hamster ovary cells. Other eukaryotic host cells such as those of filamentous fungi, plant, insect, amphibian cells or ovarian species may also be employed. Preferred host cells are prokaryotic hosts, especially bacterial hosts, commonly gram-negative bacterial hosts, particularly enterobacteriacae, preferably *E. coli*, and especially B or K12 strains thereof.

Polypeptides which can be produced by the process of the present invention include therapeutic proteins and peptides, including cytokines, growth factors, antibodies, antibody fragments, immunoglobulin like polypeptides, enzyme, vaccines, peptide hormones, such as insulin, and analogues thereof, chemokines, receptors, receptor fragments, kinases, phosphatases, isomerases, hydrolyases, transcription factors and fusion polypeptides.

Antibodies which can be expressed include monoclonal antibodies, polyclonal antibodies and antibody fragments having biological activity, including multivalent and/or multispecific forms of any of the foregoing.

Naturally occurring antibodies typically comprise four polypeptide chains, two identical heavy (H) chains and two identical light (L) chains inter-connected by disulfide bonds. Each heavy chain comprises a variable region ($V_H$) and a constant region ($C_H$), the $C_H$ region comprising in its native form three domains, $C_H1$, $C_H2$ and $C_H3$. Each light chain comprises a variable region ($V_L$) and a constant region comprising one domain, $C_L$.

The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4.

Antibody fragments which can be expressed comprise a portion of an intact antibody, said portion having a desired biological activity. Antibody fragments generally include at least one antigen binding site. Examples of antibody fragments include: (i) Fab fragments having $V_L$, $C_L$, $V_H$ and $C_H1$ domains; (ii) Fab derivatives, such as a Fab' fragment having one or more cysteine residues at the C-terminus of the $C_H1$ domain, that can form bivalent fragments by disulfide bridging between two Fab derivatives; (iii) Fd fragment having $V_H$ and $C_H1$ domains; (iv) Fd derivatives, such as Fd derivatives having one or more cysteine residues at the C-terminus of the $C_H1$ domain; (v) Fv fragments having the $V_L$ and $V_H$ domains of a single arm of an antibody; (vi) single chain antibody molecules such as single chain Fv (scFv) antibodies in which the $V_L$ and $V_H$ domains are covalently linked; (vii) $V_H$ or $V_L$ domain polypeptide without constant region domains linked to another variable domain (a $V_H$ or $V_L$ domain polypeptide) that is with or without constant region domains, (e.g., $V_H$-$V_H$, $V_H$-$V_L$, or $V_L$-$V_L$) (viii) domain antibody fragments, such as fragments consisting of a $V_H$ domain, or a $V_L$ domain, and antigen-binding fragments of either $V_H$ or $V_L$ domains, such as isolated CDR regions; (ix) so-called "diabodies" comprising two antigen binding sites, for example a heavy chain variable domain ($V_H$) connected to a light chain variable domain ($V_L$), in the same polypeptide chain; and (x) so-called linear antibodies comprising a pair of tandem Fd segments which, together with complementary light chain polypeptides, form a pair of antigen binding regions.

Preferred antibody fragments that can be prepared are mammalian single variable domain antibodies, being an antibody fragment comprising a folded polypeptide domain which comprises sequences characteristic of immunoglobulin variable domains and which specifically binds an antigen (i.e., dissociation constant of 500 nM or less, such as 400 nM or less, preferably 250 nM or less, and most preferably 100 nM or less), and which binds antigen as a single variable domain; that is, without any complementary variable domain. Single variable domain antibodies include complete antibody variable domains as well as modified variable domains, for example in which one or more loops have been replaced by sequences which are not characteristic of antibody variable domains or antibody variable domains which have been truncated or comprise N- or C-terminal extensions, as well as folded fragments of variable domains. Preferred single variable domains which can be prepared are selected from the group of $V_H$ and $V_L$, including Vkappa and Vlambda. Most preferably the single variable domains are human or camelid domains, including humanised camelid domains.

Where the target polypeptide comprises two or more chains to be secreted, particularly where the target polypeptide is a fragment antibody comprising two or more chains, each of the chains is attached to a secretion leader according to the present invention, and polynucleotides encoding such polypeptides are designed accordingly, and incorporated into the vectors employed. The secretion leaders employed may be the same or different.

In certain embodiments of the present invention, the vector expressed is a self-replicating plasmid where the promoter, operator sequence, expression cassette for the target polypeptide and terminator sequence for the expression cassette are located upstream of a multimer resolution system, preferably a cer locus. It is preferred that the ORI is located downstream of the multimer resolutions system. In many embodiments, a repressor sequence, such as a LacI repressor, preferably orientated in the opposite orientation to transcription of the expression cassette, is located downstream (when read in the direction of transcription of the expression cassette) of the ORI. Advantageously, a selectable marker, preferably a tetA/TetR marker is located downstream of the repressor sequence. Most preferably, a terminator sequence is located downstream of the selectable marker.

In some embodiments, the vector employed comprises a promoter, operator sequence, expression cassette for the target polypeptide and terminator sequence for the expression cassette which is separated, when read in the direction of transcription, from the repressor sequence by a multimer resolution sequence and, especially, additionally by the ORI.

In some embodiments, the vector employed comprises a repressor sequence separated, when read in the direction of transcription of the expression cassette for the target polypeptide, from the promoter, by a selectable marker sequence, and preferably also by a transcriptional terminator sequence downstream of the selectable marker sequence.

The expression system is expressed by methods well known in the art for the cells employed. Preferred expression methods include culturing the host cells in a culture medium, especially by fermentation, and then recovering the expressed protein. The term "culture medium" refers to a nutrient medium used for growing the recombinant cells. In many embodiments, a nutrient solution is employed. Suitable culture media for given host cells are well known in the art.

In many embodiments, the process of the present invention comprises a growth phase, where the host cells are cultured until the desired cell density is achieved, and a production phase during which the target polypeptide is expressed. Such a process is preferably employed when an inducible promoter and operator system is employed. The promoter is commonly maintained in uninduced state during the growth phase, thereby substantially preventing expression of the target polypeptide, and hence reducing the metabolic burden on the host cells. When the desired cell density is reached, expression is induced, and the target polypeptide is expressed. The growth phase is typically maintained for a number of days, such as from 1 to 10 days, and preferably from 2 to 4 days. Cell densities achieved during the growth phase are typically equivalent to an OD600 of up to 150, such as from 5 to 150, and commonly from 30-70. Once the desired cell density is reached, the cells are maintained in the production phase, preferably following induction of expression. The production phase can be carried out using continuous culture, such as in a chemostat, but is preferably carried out using fed-batch culture. The production phase is commonly maintained for up to 48 hours, such as from 12 to 36 hours when fed-batch culture is employed. At the end of a batch production phase, the target polypeptide is recovered by methods well known in the art.

In preferred embodiment of the present invention, both the growth phase and the production phase are carried out in the absence of antibiotic.

In preferred embodiments where an inducible expression system is employed, expression may be induced by the addition of the appropriate inducer, such as isopropyl-β-D-1-thiogalactopyranoside (IPTG), analogues of IPTG such as isobutyl-C-galactoside (IBCG), lactose or melibiose, or by the adjustment of conditions to cause induction, depending upon the nature of the inducible system employed. Inducers may be used individually or in combination.

The polypeptide produced by the process of the present invention may be subjected to further purification steps if desired, for example one or more of ion exchange chromatography; chromatography based on hydrophobicity, such as HIC, reverse phase chromatography, hydrophobic charge induction chromatography, or mixed mode chromatography; or size-based purifications such as gel filtration.

According to one preferred embodiment of the present invention, there is provided a process for the production of a target recombinant polypeptide which comprises:

a) growing a prokaryote host cell, especially *E. coli*, transformed with a vector comprising:
  i) an inducible promoter operatively linked to an expression cassette for the target recombinant polypeptide; and
  ii) a perfect palindrome operator sequence;
in a culture medium, until a target cell density is reached; and
b) inducing expression of the expression cassette in the presence of a culture medium;
wherein the culture medium employed in steps a) and b) is substantially free from antibiotic.

In the preferred aspect of the present invention, the vector employed is advantageously a vector comprising an IPTG-inducible promoter and operator system, especially a T7A3, tac, lac or λpL promoter with two perfect palindrome operator, preferably lac, sequences, together with the corresponding repressor sequence; and a cer multimer resolution sequence; a ColE1 ORI. In many particularly preferred embodiments, the vector additionally comprises an inducible selection marker.

The present invention is illustrated without limitation by the following examples.

Example 1

Strain CLD178 was constructed by cloning a sequence encoding human G-CSF (Granulocyte Colony Stimulating Factor) having the sequence:

(Sequence ID No. 1)
CATATGACTCCACTGGGTCCTGCTTCTTCTCTGCCTCAATCTTTTCTGCT

GAAATGTCTGGAACAGGTTCGTAAAATCCAGGGTGATGGTGCGGCACTGC

AGGAGAAACTGTGCGCGACGTACAAACTGTGCCACCCGGAGGAGCTGGTT

CTGCTGGGCCACTCCCTGGGCATCCCATGGGCACCGCTGTCCTCTTGCCC

GTCTCAGGCCCTGCAACTGGCAGGTTGCCTGTCTCAGCTGCACTCTGGCC

TGTTCCTGTATCAGGGTCTGCTGCAAGCGCTGGAAGGCATTTCCCCGGAA

CTGGGTCCGACCCTGGACACCCTGCAGCTGGACGTCGCGGACTTCGCAAC

GACCATCTGGCAGCAGATGGAAGAGCTGGGTATGGCTCCGGCACTGCAGC

CGACTCAGGGTGCAATGCCGGCCTTTGCCAGCGCGTTCCAGCGCCGTGCT

GGCGGTGTACTGGTTGCGTCTCACCTGCAGTCTTTTCTGGAGGTTTCCTA

CCGCGTGCTGCGCCATCTGGCTCAGCCTTGATAACTCGAG into vector pAVE011 (prepared as described in International patent application WO2007/088371) using Nde I and Xho I to clone the sequence into the vector. The resulting plasmid was transformed into *E. coli* W3110 to create strain CLD178. In addition the gene was also cloned by the same method into pET29a (Novagen), which was transformed into BL21(λDE3) to create strain CLD557.

Condensed Shake-Flask Protocol

Overnight cultures were prepared by adding 15 μl of a glycerol stock of strains CLD178 and CLD557 to 50 ml Falcon tubes containing 15 mls of Luria Broth (LB) medium and antibiotic (10 μg/ml tetracycline for CLD178; 50 μg/ml kanamycin for CLD557). These were incubated at 37° C. overnight. Antibiotic was present in this preparatory stage to ensure the presence of the expression plasmid in the host cells at the start of the antibiotic-free stages. 15 μl of each of these overnight cultures were used to inoculate duplicate fresh tubes containing 15 ml LB (without antibiotic).

The cultures were grown at 37° C. to an OD600 of 0.4 to 0.6. One sample of each culture was induced with 1 mM IPTG, one sample being left uninduced. After 8 hours total incubation, samples were taken and streaked out onto Luria agar for single colonies. 15 μl of the culture was used to inoculate a fresh culture of LB and incubated overnight. This process was repeated over 4 days.

Analysis

Plasmid retention was analysed by streaking 40 colonies from the Luria agar plates grown overnight at 37° C. onto Luria agar plus the relevant antibiotic, incubating these plates overnight at 37° C. and counting the colonies.

Figure 1:
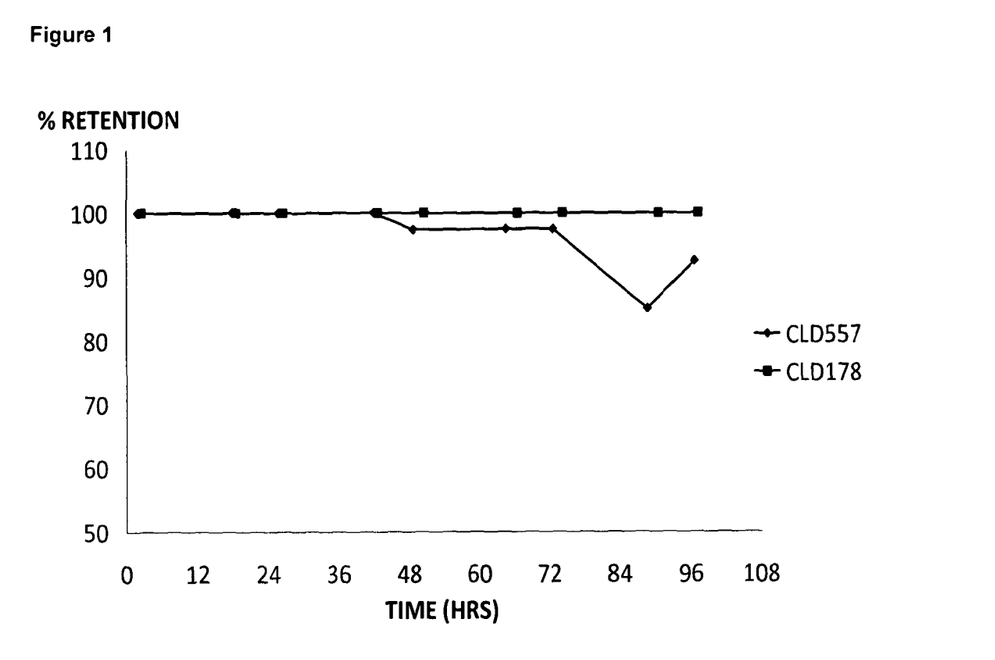
Figure 2:
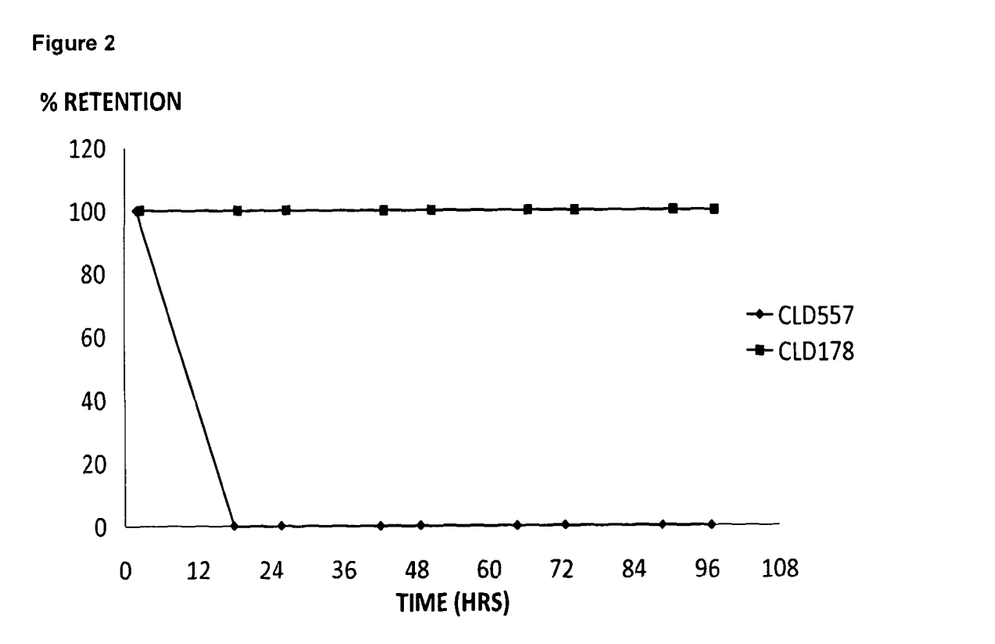

The results achieved, expressed as a percentage of the colonies containing the plasmid are given in plotted in FIGS. 1 and 2.

The results in FIG. 1 show that, in the absence of an antibiotic in the culture medium, for the pET-containing strain, CLD557, loss of plasmid starts to occur after 48 hours and continues towards the end of the growth phase at 96 hours, even in an uninduced state, whereas the strain containing the vector as employed in the process of present invention, CLD178, is stable throughout the growth phase, giving 100% stability even after 96 hours.

The results in FIG. 2 show that when the expression of the target polypeptide is induced in the production phase, in the absence of antibiotic, the pET vector is rapidly lost, with no plasmid recovered after 18 hours, whereas the strain containing the vector as employed in the process of present invention is stable throughout the production phase giving 100% stability even after 96 hours.

The process according to the present invention demonstrates that the process of the present invention is highly suited to the production of polypeptides in antibiotic-free culture processes, and shows much superior plasmid stability than the well known pET-type plasmid.

Example 2

Strain CLD179 was prepared by the method given above for CLD178, except that a polynucleotide coding for human growth hormone was employed, having the sequence:

(Sequence ID No. 2)
CATATGTTTCCAACTATCCCACTGTCTCGTCTGTTTGATAATGCTATGCT

GCGCGCCCACCGTCTGCATCAACTGGCCTTCGATACCTACCAGGAATTTG

AGGAGGCGTACATTCCAAAAGAACAGAAATACTCTTTCCTGCAGAATCCG

CAGACCTCTCTGTGCTTCAGCGAATCCATCCCTACTCCTTCTAACCGCGA

GGAAACCCAGCAAAAGAGCAACCTGGAACTGCTGCGTATCTCCCTGCTGC

TGATCCAGAGCTGGCTGGAGCCGGTTCAGTTTCTGCGTTCCGTGTTCGCG

AATTCCCTGGTGTATGGCGCCTCCGACTCCAACGTTTACGACCTGCTGAA

AGACCTGGAAGAGGGCATCCAGACTCTGATGGGCCGTCTGGAGGACGGCT

CCCCTCGTACCGGCCAGATCTTCAAACAAACCTACAGCAAATTTGATACC

AACAGCCACAATGACGACGCTCTGCTGAAAAACTACGGCCTGCTGTACTG

TTTCCGCAAGGATATGGATAAAGTAGAAACCTTTCTGCGCATCGTTCAAT

GTCGCAGCGTGGAAGGTAGCTGCGGCTTCTGATAACTCGAG

When subjected to the condensed shake flask protocol and analysis as described in Example 1, plasmid recovery of 40% after 66 hours was recorded.

Examples 3, 4 and 5

Strains CLD604 and CLD605 were prepared by the methods given above in Example 1 and 2, respectively, except that a polynucleotide of Sequence ID No. 3 coding for the pBR322 origin of replication including rop, was prepared as an AhdI/Bpu10I fragment. This fragment was cloned into the corresponding vectors using the AhdI and Bpu10I restriction sites in the vector, thus replacing the original plasmid based origin of replication.

```
Sequence ID No. 3:
CCTGAGCGCATGTTCATCATCAGTAACCCGTATCGTGAGCATCCTCTCT
CGTTTCATCGGTATCATTACCCCCATGAACAGAAATCCCCCTTACACGG
AGGCATCAGTGACCAAACAGGAAAAAACCGCCCTTAACATGGCCCGCTT
TATCAGAAGCCAGACATTAACGCTTCTGGAGAAACTCAACGAGCTGGAC
GCGGATGAACAGGCAGACATCTGTGAATCGCTTCACGACCACGCTGATG
AGCTTTACCGCAGCTGCCTCGCGCGTTTCGGTGATGACGGTGAAAACCT
CTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGT
GTCGGGGCGCAGCCATGACCCAGTCACGTAGCGATAGCGGAGTGTATAC
TGGCTTAACTATGCGGCATCAGAGCAGATTGTACTGAGAGTGCACCATA
TGCGGTGTGAAATACCGCACAGATGCGTAAGGAGAAAATACCGCATCAG
GCGCTCTTCCGCTTCCTCGCTCACTGACTCGCTGCGCTCGGTCGTTCGG
CTGCGGCGAGCGGTATCAGCTCACTCAAAGGCGGTAATACGGTTATCCA
CAGAATCAGGGGATAACGCAGGAAAGAACATGTGAGCAAAAGGCCAGCA
AAAGGCCAGGAACCGTAAAAAGGCCGCGTTGCTGGCGTTTTTCCATAGG
CTCCGCCCCCCTGACGAGCATCACAAAAATCGACGCTCAAGTCAGAGGT
GGCGAAACCCGACAGGACTATAAAGATACCAGGCGTTTCCCCCTGGAAG
CTCCCTCGTGCGCTCTCCTGTTCCGACCCTGCCGCTTACCGGATACCTG
TCCGCCTTTCTCCCTTCGGGAAGCGTGGCGCTTTCTCATAGCTCACGCT
GTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTAT
CGTCTTGAGTCCAACCCGGTAAGACACGACTTATCGCCACTGGCAGCAG
CCACTGGTAACAGGATTAGCAGAGCGAGGTATGTAGGCGGTGCTACAGA
GTTCTTGAAGTGGTGGCCTAACTACGGCTACACTAGAAGGACAGTATTT
GGTATCTGCGCTCTGCTGAAGCCAGTTACCTTCGGAAAAAGAGTTGGTA
GCTCTTGATCCGGCAAACAAACCACCGCTGGTAGCGGTGGTTTTTTTGT
TTGCAAGCAGCAGATTACGCGCAGAAAAAAAGGATCTCAAGAAGATCCT
TTGATCTTTTCTACGGGGTCTGACGCTCAGTGGAACGAAAACTCACGTT
AAGGGATTTTGGTCATGAGATTATCAAAAAGGATCTTCACCTAGATCCT
TTTAAATTAAAAATGAAGTTTTAAATCAATCTAAAGTATATATGAGTAA
ACTTGGTCTGACAGTTACCAATGCTTAATCAGTGAGGCACCTATCTCAG
CGATCTGTCTATTTCGTTCATCCATAGTTGCCTGACTCCCCGTC
```

Recombinant clones were identified by restriction digest and confirmed by sequencing.

Strain CLD607 was prepared by the same method given for Strain CLD604, except that a polynucleotide of Sequence ID No. 4 coding for the p15a origin of replication was prepared as an AhdI/Bpu10I fragment.

```
Sequence ID No. 4:
CCTGAGCGCGCTAGCGGAGTGTATACTGGCTTACTATGTTGGCACTGAT
GAGGGTGTCAGTGAAGTGCTTCATGTGGCAGGAGAAAAAAGGCTGCACC
GGTGCGTCAGCAGAATATGTGATACAGGATATATTCCGCTTCCTCGCTC
ACTGACTCGCTACGCTCGGTCGTTCGACTGCGGCGAGCGGAAATGGCTT
ACGAACGGGGCGGAGATTTCCTGGAAGATGCCAGGAAGATACTTAACAG
GGAAGTGAGAGGGCCGCGGCAAAGCCGTTTTTCCATAGGCTCCGCCCCC
CTGACAAGCATCACGAAATCTGACGCTCAAATCAGTGGTGGCGAAACCC
GACAGGACTATAAAGATACCAGGCGTTTCCCCTGGCGGCTCCCTCGTGC
GCTCTCCTGTTCCTGCCTTTCGGTTTACCGGTGTCATTCCGCTGTTATG
GCCGCGTTTGTCTCATTCCACGCCTGACACTCAGTTCCGGGTAGGCAGT
TCGCTCCAAGCTGGACTGTATGCACGAACCCCCCGTTCAGTCCGACCGC
TGCGCCTTATCCGGTAACTATCGTCTTGAGTCCAACCCGGAAAGACATG
CAAAAGCACCACTGGCAGCAGCCACTGGTAATTGATTTAGAGGAGTTAG
TCTTGAAGTCATGCGCCGGTTAAGGCTAAACTGAAAGGACAAGTTTTGG
TGACTGCGCTCCTCCAAGCCAGTTACCTCGGTTCAAAGAGTTGGTAGCT
CAGAGAACCTTCGAAAAACCGCCCTGCAAGGCGGTTTTTTCGTTTTCAG
AGCAAGAGATTACGCGCAGACCAAAACGATCTCAAGAAGATCATCTTAT
TAATCAGATAAAATATTTCTAGATTTCAGTGCAATTTATCTCTTCAAAT
GTAGCACCTGAAGTCAGCCCCATACGATATAAGTTGTAGACTCCCCGTC
```

When subjected to the condensed shake flask protocol and analysis as described in Example 1, plasmid recovery after 66.5 hours were as given in Table 1.

TABLE 1

| Strain | Recovery (%) |
| --- | --- |
| CLD604 | 100 |
| CLD605 | 88 |
| CLD607 | 90 |

Example 6

CLD579 (pAVE446)

The cer locus was removed from pAVE175 as a BglII/ClaI fragment. Plasmid fragment overhangs were blunted in a PCR reaction with KOD Hot Start DNA polymerase (Novagen, 71086-3, lot M00050873) and ligated to reform the plasmid. Recombinant clones were identified by restriction digest and confirmed by sequencing. The resultant plasmid was named pAVE446 and transformed into CGSC4474. An equal amount of overnight culture was mixed with 40% glycerol and aliquoted into cryovials for storage at −70° C.

When subjected to the condensed shake flask protocol and analysis as described in Example 1, plasmid recoveries of 83% after 28 hours, and 43% after 52 hours were recorded, showing greater recoveries than those achieved for pET in Example 1.

Examples 7 & 8

Strain CLD722 was prepared by inserting a polynucleotide of Sequence ID No. 5 into the vector employed to prepare Strain CLD178 above. The polynucleotide represents a portion of the vector backbone, but lacking the T4 terminator sequence, as an XmaI/EcoRI fragment, and was inserted into the XmaI and EcoRI restriction sites in the vector.

```
                                            Sequence ID No. 5
CCCGGGGCATGACCGTCGTCGCCGCCCTGATGGCGGTCTTCTTCATCATG

CAACTTGTCGGACAGGTGCCGGCCGCGCTTTGGGTCATTTTCGGCGAGGA

TCGCTTTCACTGGGACGCGACCACGATCGGCATTTCGCTTGCCGCATTTG

GCATTCTGCATTCACTCGCCCAGGCAATGATCACCGGCCCTGTAGCCGCC

CGGCTCGGCGAAAGGCGGGCACTCATGCTCGGAATGATTGCCGACGGCAC

AGGCTACATCCTGCTTGCCTTCGCGACACGGGATGGATGGCGTTCCCGA

TCATGGTCCTGCTTGCTTCGGGTGGCATCGGAATGCCGGCGCTGCAAGCA

ATGTTGTCCAGGCAGGTGGATGAGGAACGTCAGGGGCAGCTGCAAGGCTC

ACTGGCGGCGCTCACCAGCCTGACCTCGATCGTCGGACCCCTCCTCTTCA

CGGCGATCTATGCGGCTTCTATAACAACGTGGAACGGGTGGGCATGGATT

GCAGGCGCTGCCCTCTACTTGCTCTGCCTGCCGGCGCTGCGTCGCGGGCT

TTGGAGCGGCGCAGGGCAACGAGCCGATCGCTGATCGTGGAAACGATAGG

CCTCCATGTGGGAATTGTGAGCGCTCACAATTCCAAGAACAATCCTGCAC

GAATTC
```

Strain CLD724 was prepared by the method given in Example 1, except that the vector employed was prepared by cloning a polynucleotide of Sequence ID No. 5 into the XmaI and EcoRI restriction sites of vector pAVE011, and by cloning a polynucleotide of Sequence ID No. 2 into the Nde I and Xho I restriction sites in that vector.

When subjected to the condensed shake flask protocol and analysis as described in Example 1, plasmid recovery after 74 hours were as given in Table 2.

TABLE 2

| Strain | Recovery (%) |
|---|---|
| CLD722 | 100 |
| CLD724 | 92.5 |

Examples 9 and 10

Fermentation inocula for the strains CLD178 and CLD048 (prepared as described in WO 2007/088371, expressing the Fab D1.3) were raised by adding 450 µl of glycerol stock to a 2.0 L baffled shake flask containing 450 mL of Luria Broth (LB) containing 5 g/L yeast extract, 10 g/L peptone, 10 g/L sodium chloride, 10 g/L glucose and 15 mg/L tetracycline, where appropriate. Inocula were grown for 10 h at 37° C. in a shaker-incubator with an agitation of 200 rpm. 20 ml of shake flask inoculum was used to inoculate a 5 L working volume fermenter containing 4 L of minimal glycerol batch growth medium supplemented with yeast extract and tetracycline (as appropriate). The fermentation was carried out under the operating conditions described below. Temperature was controlled either at a constant temperature of 37° C. (CLD178) or at 37° C. for the first 7-9 hours then reduced to 30° C. and controlled at 30° C. for the remainder of the fermentation (CLD048). pH was controlled at 7.0 by automatic addition of 25% (w/v) ammonium hydroxide. The dissolved oxygen tension (dOT) set point was 30% of air saturation and was controlled by automatic adjustment of the fermenter stirrer speed, from a minimum of 250 rpm up to a maximum of 1500 rpm, and supplementation of oxygen to the inlet gas stream. Airflow to the fermenter vessel was 0.5 v/v/min throughout.

Fermentations were performed in batch mode until depletion of the carbon source (i.e. glycerol) which was characterized by a sharp rise in dOT. Fed-batch fermentation was initiated at the point of carbon source exhaustion by the addition of a glycerol/ammonium sulphate feed. Induction was carried out by addition of IPTG to a final concentration of 0.5 mM (CLD178) or 0.125 mM (CLD048) once the biomass level in the fermentation reached OD600=45-55. The fed-batch phase was continued for 48 hrs post induction. The cells and residual cell free growth medium were then harvested. The harvested cells for CLD048 were further subjected to osmotic shock cell fractionation to isolate the cellular fraction containing proteins that had partitioned in the soluble E. coli periplasmic fraction. The cells from the CLD178 fermentation were analysed directly by SDS-PAGE.

Analytical Methods

The accumulation levels for G-CSF from CLD178 were determined using SimplyBlue stained SDS-PAGE gels of whole cell lysates of the samples.

The accumulation of biologically active D1.3 Fab in the soluble periplasmic extract and residual growth medium was estimated by determining the binding of D1.3 Fab to lysoszyme (antigen) in an ELISA assay by reference to a standard curve prepared with purified active D1.3 Fab.

Results

CLD178

Analysis of the fermentation broth showed 100% plasmid retention from both fermentations at each of shake flask, pre-induction and end of fermentation, in both presence and absence of antibiotic SDS-PAGE analysis showed no difference in yield of G-CSF at the end of fermentation either in the presence or absence of antibiotic.

CLD048

After 27 hours post-induction, the quantity of D1.3 as measured by ELISA was 309 mg/L for the antibiotic free process compared with 250 mg/L for the process containing antibiotic. At 48 hours post-induction, the quantity of D1.3 as measured by ELISA was 205 mg/L for the antibiotic free process compared with 208 mg/L for the process containing antibiotic. These results indicate no effect on overall yield for the antibiotic free process compared with the fermentation in the presence of antibiotic.

The invention claimed is:

1. A process of producing a non-essential target recombinant polypeptide which comprises:
   (a) growing a prokaryotic host cell transformed with a vector comprising an inducible promoter operatively linked to both (i) a perfect palindrome operator sequence and (ii) an expression cassette for the target recombinant polypeptide without inducing the expression of the expression cassette until a target cell density is reached in a culture medium without an inducer inducing the expression; and
   (b) inducing the expression of the expression cassette in the presence of a culture medium with an inducer inducing the expression;
wherein the culture medium employed in steps (a) and (b) is free from antibiotic.

2. The process according to claim 1, wherein the promoter is selected from the group consisting of T7A3, tac, lac and λpL promoters.

3. The process according to claim 1, wherein the vector comprises one or more of:
   (a) a multimer resolution system;
   (b) a colE1 ORI;
   (c) two perfect palindrome operators; and/or
   (d) an antibiotic resistance marker.

4. The process according to claim 1, wherein the vector additionally comprises a transcriptional terminator sequence for the expression cassette and a multimer resolution system, the promoter, operator sequence, expression cassette for the target polypeptide and transcriptional terminator sequence for the expression cassette being located upstream of the multimer resolution system.

5. The process according to claim 4, wherein the vector comprises an ORI, located downstream of the multimer resolutions system.

6. The process according to claim 5, wherein the vector comprises a repressor sequence located downstream of the ORI.

7. The process according to claim 6, wherein the vector comprises a selectable marker located downstream of the repressor sequence.

8. The process according to claim 3, wherein the vector comprises a transcriptional terminator sequence for the expression cassette, a multimer resolution sequence and a repressor sequence, and wherein the promoter, operator sequence, expression cassette for the target polypeptide and transcriptional terminator sequence for the expression cassette are separated, when read in the direction of transcription, from the repressor sequence by the multimer resolution sequence.

9. The process according to claim 3, wherein the vector comprises a repressor sequence, a selectable marker system and a transcriptional terminator sequence, the repressor sequence being separated, when read in the direction of transcription of the expression cassette for the target polypeptide, from the promoter, by the selectable marker sequence, and also by the transcriptional terminator sequence downstream of the selectable marker sequence.

10. The process according to claim 3, wherein the promoter is selected from the group consisting of T7A3, tac, lac and λpL promoters.

11. The process according to claim 4, wherein the vector comprises a transcriptional terminator sequence for the expression cassette, a multimer resolution sequence and a repressor sequence, and wherein the promoter, operator sequence, expression cassette for the target polypeptide and transcriptional terminator sequence for the expression cassette are separated, when read in the direction of transcription, from the repressor sequence by the multimer resolution sequence.

12. The process according to claim 4, wherein the vector comprises a repressor sequence, a selectable marker system and a transcriptional terminator sequence, the repressor sequence being separated, when read in the direction of transcription of the expression cassette for the target polypeptide, from the promoter, by the selectable marker sequence, and also by the transcriptional terminator sequence downstream of the selectable marker sequence.

13. The process according to claim 12, wherein the vector comprises a repressor sequence, a selectable marker system and a transcriptional terminator sequence, the repressor sequence being separated, when read in the direction of transcription of the expression cassette for the target polypeptide, from the promoter, by the selectable marker sequence, and also by the transcriptional terminator sequence downstream of the selectable marker sequence.

14. The process according to claim 1, wherein the prokaryotic host cell is an *E. coli* prokaryotic host cell.

15. A process of producing a non-essential target recombinant polypeptide which comprises:
   (a) growing a prokaryotic host cell transformed with a vector comprising an inducible promoter operatively linked to both (i) a perfect palindrome operator sequence and (ii) an expression cassette for the target recombinant polypeptide in a culture medium until a target cell density is reached; and
   (b) inducing the expression of the expression cassette in the presence of a culture medium;
   wherein the culture medium employed in steps (a) and (b) is free from antibiotic.

16. The process according to claim 15, wherein the promoter is selected from the group consisting of T7A3, tac, lac and λpL promoters.

17. The process according to claim 15, wherein the vector comprises one or more of:
   (a) a multimer resolution system;
   (b) a colE1 ORI;
   (c) two perfect palindrome operators; and/or
   (d) an antibiotic resistance marker.

18. The process according to claim 15, wherein the vector additionally comprises a transcriptional terminator sequence for the expression cassette and a multimer resolution system, the promoter, operator sequence, expression cassette for the target polypeptide and transcriptional terminator sequence for the expression cassette being located upstream of the multimer resolution system.

19. The process according to claim 18, wherein the vector comprises an ORI, located downstream of the multimer resolutions system.

20. The process according to claim 19, wherein the vector comprises a repressor sequence located downstream of the ORI.

* * * * *